(12) United States Patent
Bolmsjö

(10) Patent No.: US 6,868,290 B2
(45) Date of Patent: Mar. 15, 2005

(54) THERMOTHERAPY CATHETER AND METHOD OF PROSTATE THERMOTHERAPY WITH IMPROVED GUIDE AND HEAT CONFINEMENT

(75) Inventor: Magnus Bolmsjö, Lund (SE)

(73) Assignee: Prostalund Operations AB, Lund (SE)

( * ) Notice: Subject to any disclaimer, the term of this patent is extended or adjusted under 35 U.S.C. 154(b) by 154 days.

(21) Appl. No.: 10/428,700

(22) Filed: May 2, 2003

(65) Prior Publication Data

US 2003/0195595 A1 Oct. 16, 2003

Related U.S. Application Data

(63) Continuation of application No. 09/979,854, filed on Nov. 5, 2001, now Pat. No. 6,584,361.

(51) Int. Cl.[7] .................................................. A61F 7/00
(52) U.S. Cl. ....................................... 607/101; 607/102
(58) Field of Search ............................ 607/96, 99–102, 607/104–105

(56) References Cited

U.S. PATENT DOCUMENTS

| | | |
|---|---|---|
| 4,204,549 A | 5/1980 | Paglione |
| 4,311,154 A | 1/1982 | Sterzer et al. |
| 4,676,258 A | 6/1987 | Inokuchi et al. |
| 4,967,765 A | 11/1990 | Turner et al. |
| 5,084,044 A | 1/1992 | Quint |
| 5,159,925 A | 11/1992 | Neuwirth et al. |
| 5,234,004 A | 8/1993 | Hascoet et al. |
| 5,257,977 A | 11/1993 | Eshel |
| 5,366,490 A | 11/1994 | Edwards et al. |
| 5,421,819 A | 6/1995 | Edwards et al. |
| 5,464,445 A | 11/1995 | Rudie et al. |
| 5,480,417 A | 1/1996 | Hascoet et al. |
| 5,623,940 A | 4/1997 | Daikuzono |
| 5,645,528 A | 7/1997 | Thome |
| 5,861,021 A | 1/1999 | Thome et al. |
| 5,931,860 A | 8/1999 | Reid et al. |
| 5,964,791 A | 10/1999 | Bolmsjö |
| 6,223,085 B1 | 4/2001 | Dann et al. |
| 6,496,737 B2 | 12/2002 | Rudie et al. |

FOREIGN PATENT DOCUMENTS

| | | |
|---|---|---|
| JP | 2121675 | 5/1990 |
| SE | 9502523-5 | 1/1997 |
| WO | WO9309724 | 5/1993 |
| WO | WO94017177 | 1/1994 |
| WO | WO9519142 | 7/1995 |
| WO | WO9636288 | 11/1996 |
| WO | WO9702794 | 1/1997 |
| WO | WO9907325 | 2/1999 |
| WO | WO9917689 | 4/1999 |
| WO | WO0045758 | 8/2000 |

*Primary Examiner*—Roy D. Gibson
(74) *Attorney, Agent, or Firm*—John R. Ley

(57) ABSTRACT

A thermotherapy catheter for heat treating the prostate gland includes an O-ring positioned within a chamber between an outer tube and an interior heat generation device guide tube. The O-ring supports a distal end portion of a probe guide tube at a desired acute angle so that a temperature probe can be advanced from the end of the probe guide tube into the prostate gland at a predetermined desired acute angle for calculating tissue heating and tissue necrosis information from temperature sensors located on a distal end of the temperature probe. The O-ring also separates a still liquid chamber from a circulatory flow path so that heated liquid surrounding the generation device is applied effectively to heat the prostate gland, while the circulating cooling fluid effectively removes heat from a feed cable which supplies energy to the heat generation device.

20 Claims, 3 Drawing Sheets

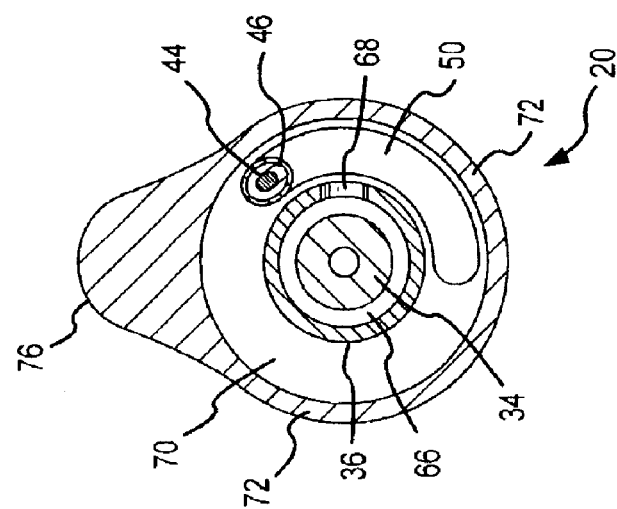
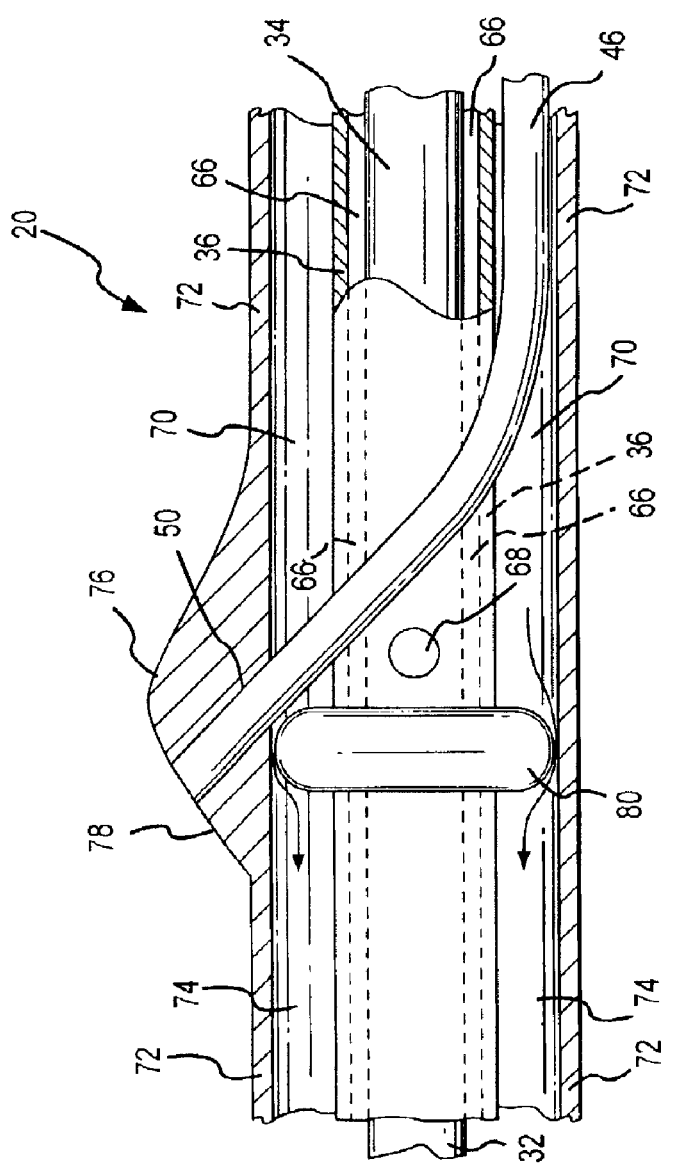
FIG.2
FIG.3

THERMOTHERAPY CATHETER AND METHOD OF PROSTATE THERMOTHERAPY WITH IMPROVED GUIDE AND HEAT CONFINEMENT

CROSS-REFERENCE TO RELATED APPLICATION

This is a continuation in part of U.S. patent application Ser. No. 09/979,854, filed Nov. 5, 2001, for a Method and Device for Heat Treatment of Body Tissue, now U.S. Pat. No. 6,584,361 issued Jun. 24, 2003.

FIELD OF THE INVENTION

This invention relates to thermotherapy treatment of bodily tissue, such as microwave thermotherapy of the prostate gland. More particularly, the present invention relates to a new and improved catheter which employs an O-ring structure within the catheter to guide a temperature probe into a predetermined position within the tissue such as a prostate gland to assure predictable interpretation and evaluation of the thermotherapy treatment. The O-ring structure of the new and improved catheter further assists confining heat generated within the catheter to the tissue where treatment is intended. In addition, the present invention more particularly relates to a new and improved thermotherapy treatment of the prostate gland which makes use of a catheter using the O-ring structure.

BACKGROUND OF THE INVENTION

Malignant and benign growth of the prostate gland typically cause urinary problems. Benign prostate hyperplasia (BPH) is a benign growth within the prostate gland which causes an obstruction that constricts the urinary canal or prostatic urethra, thereby restricting urine flow and making urination difficult, painful, or in aggravated circumstances, almost impossible. At various levels of severity, BPH afflicts a significant percentage of the older male population. Malignant cancer of the prostate gland may also create similar urination problems, but more significantly, malignant prostate cancer may spread to other tissues unless eradicated.

Thermotherapy is a treatment where bodily tissue is subjected to heat at a temperature high enough for a long enough period of time to cause tissue death or necrosis while coagulating blood flow into the dead tissue. In the treatment of BPH, thermotherapy is used to kill a limited amount of the prostate gland surrounding the prostatic urethra, without destroying the entire prostate gland. As the dead tissue sloughs off after treatment and the prostatic urethra grows back, a larger urinary canal exists through the prostate gland to permit urine flow without obstruction or significant pain. In the treatment of malignant prostate gland cancer, it is desirable for the thermotherapy to kill only the malignant cancerous tissue, while preserving the adjoining healthy tissue.

Typical sources of heat used for prostate thermotherapy include microwave radiation, radio frequency energy, laser energy, and hot liquid. Microwave energy is a very effective thermotherapy energy source for treatment of prostate gland disease. The microwave energy is delivered from a microwave antenna located adjacent to the prostate gland. The microwave antenna is connected by a microwave feed cable to a microwave generator. The microwave generator supplies the energy through the coaxial cable to the antenna, and the energy radiates from the antenna into the adjoining tissue. The tissue is heated in accordance with the amount of microwave energy delivered from the antenna and the pattern of radiation emitted from the antenna, called the specific absorption rate or SAR.

The quality of the thermotherapy treatment, and the physiological outcome from the treatment, is greatly enhanced by providing usable information concerning the degree of heat treatment and the progress of tissue necrosis during the treatment. The assignee of the present invention has developed a prostatic treatment catheter which permits a temperature probe containing temperature sensors to be inserted into the prostate gland and the adjoining tissue. This type of urinary catheter is described in U.S. reissue Pat. No. Re 38,299. The temperature information obtained from within the treated and adjoining tissue is interpreted and processed to inform the surgeon of the progress and degree of tissue necrosis during the treatment. U.S. Pat. No. 6,445,957, also assigned to the assignee hereof, describes more about interpreting and presenting the information from the temperature sensors inserted into the tissue.

To obtain the most reliable information concerning the extent in progress of the thermotherapy treatment, the temperature probe which carries the temperature sensors should project into the prostate gland or other treated tissue at a particular location and at an anticipated angular relationship to the urethra. With the temperature probe penetrating into the prostate gland at the anticipated location and angle, the temperature sensors occupy a predetermined relationship with the SAR energy pattern radiated into the prostate gland. That predetermined relationship permits the temperature readings to be used for reliable calculations of the extent and progress of the tissue necrosis as well as the temperature distribution within the prostate gland as the treatment progresses. If the temperature probe penetrates into the adjoining tissue at an unanticipated angle, the information derived concerning the progress of the treatment is not as accurate.

To establish the predetermined location for insertion of temperature probe, a typical inflatable balloon is located at the forward or distal end of the catheter. The catheter is inserted from a proximal exterior location of the patient through the urethra until the balloon is located within the bladder. To be inserted through the full length of the urethra into the bladder, the catheter must be made of relatively flexible materials. Once the distal end is positioned in the bladder, the balloon is inflated, and the catheter is pulled proximally or outward to seat the inflated balloon against the neck of the bladder. A probe guide tube for the temperature probe extends from the proximal end of the catheter to a location proximally spaced from the balloon. The temperature probe moves through and out of the probe guide tube and into the prostate tissue at the location proximally spaced from the balloon where the probe guide tube opens into the side of the catheter. Thus, the location where the temperature probe penetrates the tissue is established by the relationship of the distal end of the probe guide tube within the catheter relative to the balloon.

The angle which the temperature probe penetrates into the adjacent tissue is established by the angle of the probe guide tube at its distal end relative to the axis of the catheter. The catheter includes structural elements to maintain the probe guide tube at the predetermined angle. However, because the catheter must be made of flexible materials to permit insertion within the urethra, the structural elements for supporting an orienting the distal end of the probe guide tube at the predetermined angle must also be also somewhat flexible. The flexibility of the guide support structural elements can cause unintended variations in the penetration angle of the temperature probe. Maintaining the angle of the distal end of the probe guide tube is also somewhat complicated by the relatively narrow transverse width of the catheter itself. The relatively narrow transverse width tends to limit the degree of angulation of the probe guide tube near its distal end relative to the axis of the catheter. The limitation on the degree of angulation has the effect of exaggerating variations in the penetration angle which result from relatively small influences of flexibility of the catheter. While different probe guide tube support structures have been devised to attempt to preserve the predetermined angular relationship of the distal end of the probe guide tube, those structures must not significantly interfere with the flexibility of the catheter, because flexibility is required for inserting the catheter in the urethra.

Maintaining the angular orientation of the distal end of the probe guide tube is also complicated by a hollow concentric chamber or passageway which surrounds the coaxial cable that feeds microwave energy to the antenna. Inherent and unavoidable energy losses in the coaxial cable extending between the microwave generator and the microwave antenna have the potential to generate enough heat from the coaxial cable to damage the healthy tissues in the urethra and penis which are adjacent to the coaxial cable. To eliminate or reduce the risks of this undesirable heat transfer and damage to healthy tissue, cooling liquid is circulated around the coaxial cable. Circulating cooling liquid around the coaxial cable removes the heat generated by the losses in the coaxial cable and prevents undesired damage to the surrounding healthy urethra and penis.

On the other hand, it is desirable to concentrate as much heat as possible at the location where tissue destruction is desired. To this end, circulating cooling liquid around the microwave antenna is to be avoided. Instead, the heat generated by the microwave antenna should be confined within the catheter at that area so that the heat can transfer by conduction and convection into the adjoining tissue, thereby facilitating the necrosis of that tissue. The above-noted U.S. Pat. No. 6,584,361 describes the advantages of separating the cooling liquid from the heated liquid surrounding the microwave antenna. It is desirable to have the liquid surrounding the microwave antenna because the liquid more effectively matches impedance at microwave frequencies to obtain greater transmission of the microwave energy radiated from the antenna into the surrounding tissue. Since the surrounding tissue is predominantly liquid, liquid surrounding the microwave antenna provides a more continuous medium and impedance for the transfer of the radiation, than would occur if a gap or a significant amount of different type of material surrounded the microwave antenna.

The type of catheter described in the above-noted U.S. reissue Pat. No. Re 38,299 permits liquid to surround the microwave antenna but confines the circulation of cooling liquid to an area along the coaxial cable. A concentric chamber surrounds both the microwave antenna and the coaxial feed cable, but the circulation path is established only through that portion of the concentric chamber that surrounds only the coaxial feed cable. A hole extends through a tube within which the antenna and attached coaxial cable are inserted in the catheter, and the hole is located at a position proximal from the antenna at the coaxial cable. The cooling liquid enters the concentric chamber at the proximal end of the catheter, flows distally in the chamber to the location of the hole, flows through the hole, and then flows proximally in a passageway along the coaxial cable to the proximal end of the catheter. The part of the concentric chamber adjacent to the microwave antenna becomes a still liquid chamber, because liquid at that part of the concentric chamber is not within the flow path established by the location of the hole. Instead of circulating, the water in the still liquid chamber heats to a significantly higher temperature than the circulating liquid. The significantly higher temperature transfers desirable amounts of thermal energy into the adjacent tissue to assist the radiated energy in creating tissue necrosis. The heated still liquid facilitates the transfer of microwave radiation energy by establishing a continuous medium of more closely matched impedance characteristics between the antenna and the tissue.

It is with respect to these and other background considerations that the present invention has evolved.

SUMMARY OF THE INVENTION

In general, the present invention facilitates orienting and maintaining the distal end of a probe guide tube in a way that better establishes the desired predetermined angle of penetration of the temperature probe into the prostate gland and adjoining tissues. Simultaneously, the present invention assists in confining the thermal energy to the still liquid chamber surrounding the microwave antenna to facilitate thermal energy transfer into the tissue. The present invention permits the still liquid chamber to fill with liquid to achieve impedance matching and good radiant energy transfer characteristics to the surrounding tissue undergoing treatment. Moreover, the present invention achieves these improvements without compromising the flexibility of the catheter, while making the manufacture and assembly of the microwave thermotherapy catheter more cost-effective and convenient to obtain these improvements.

These and other improvements are obtained from a thermotherapy catheter having the following characteristics. An elongated outer tube extends from a proximal location of the catheter to a distal end of the catheter. A device guide tube is positioned within the outer tube and is separated from the outer tube by an annulus-like chamber. The device guide tube also extends from the proximal location to the distal end and defines an interior space for accepting a heat generation device and a connected feed cable. The device guide tube positions the heat generation device adjacent to the distal end of the catheter with the feed cable extending proximally from the heat generation device through the device guide tube to the proximal location of the catheter. The feed cable is separated from the device guide tube by an annulus-like passageway, and an opening extends through the device guide tube to create a flow path between the chamber and the passageway at a predetermined location located near a distal end of the feed cable. The opening permits circulation of a cooling liquid within the chamber from the proximal location of the catheter and through the opening and into the passageway and from the passageway to the proximal location of the catheter. A probe guide tube is located within the chamber and extends from the proximal location to an exit position located proximal from the distal end of the catheter at approximately the location of the connection of the heat generation device to the feed cable. The probe guide tube defines an interior space within which to receive an elongated temperature probe. The temperature probe is movable within the probe guide tube and includes a tip end which is movable out of the probe guide tube at the exit position. A distal end portion of the probe guide tube portion angles transversely within the chamber to establish an acute angle relative to the longitudinal extent of the catheter. The tip end of the temperature probe moves out of the catheter at the exit position at the acute angle. An important aspect of the catheter is a contact member. The contact member is positioned within the chamber at a position distal of the opening and extends between the device guide tube and the outer tube. The contact member is further positioned to contact the distal end portion of the probe guide tube at a location adjacent the exit position.

The contact of the contact member with the distal end portion of the probe guide tube supports the distal end portion of the probe guide tube to maintain the established acute angle. The support available from the contact member, which is preferably an O-ring, is particularly effective once a heat generation device and its connected feed cable are inserted within the device guide tube. The contact member further separates the chamber into a still liquid chamber located distally of the contact member and a flow path for the cooling liquid located proximally of the contact member. Liquid from the cooling liquid flow path moves past the contact member and fills the still liquid chamber. The contact member establishes a thermal barrier between the heated liquid in the still liquid chamber and the cooling liquid in the flow path, to enhance the heat treatment of the prostate gland by delivering heat from the confined and heated liquid within the still liquid chamber. Preferably the heat treatment is accomplished by microwave radiation delivered from a microwave antenna and supplied with electrical energy from a connected coaxial cable.

Another improvement available from the present invention relates to a method of heat treating the prostate gland by using a catheter, a heat generation device and connected feed cable, a temperature probe, and a flow of circulating cooling liquid in accordance with the above-described or other similar and related characteristics.

A more complete appreciation of the present disclosure and its scope, and the manner in which it achieves the above noted improvements, can be obtained by reference to the following detailed description of presently preferred embodiments taken in connection with the accompanying drawings, which are briefly summarized below, and the appended claims.

BRIEF DESCRIPTION OF THE DRAWINGS

FIG. 2 is an enlarged transverse cross section view taken substantially in the plane of line 2—2 of FIG. 1.

FIG. 3 is an enlarged view of a portion of FIG. 1, with certain elements shown in FIG. 1 eliminated.

DETAILED DESCRIPTION

Figure 1:
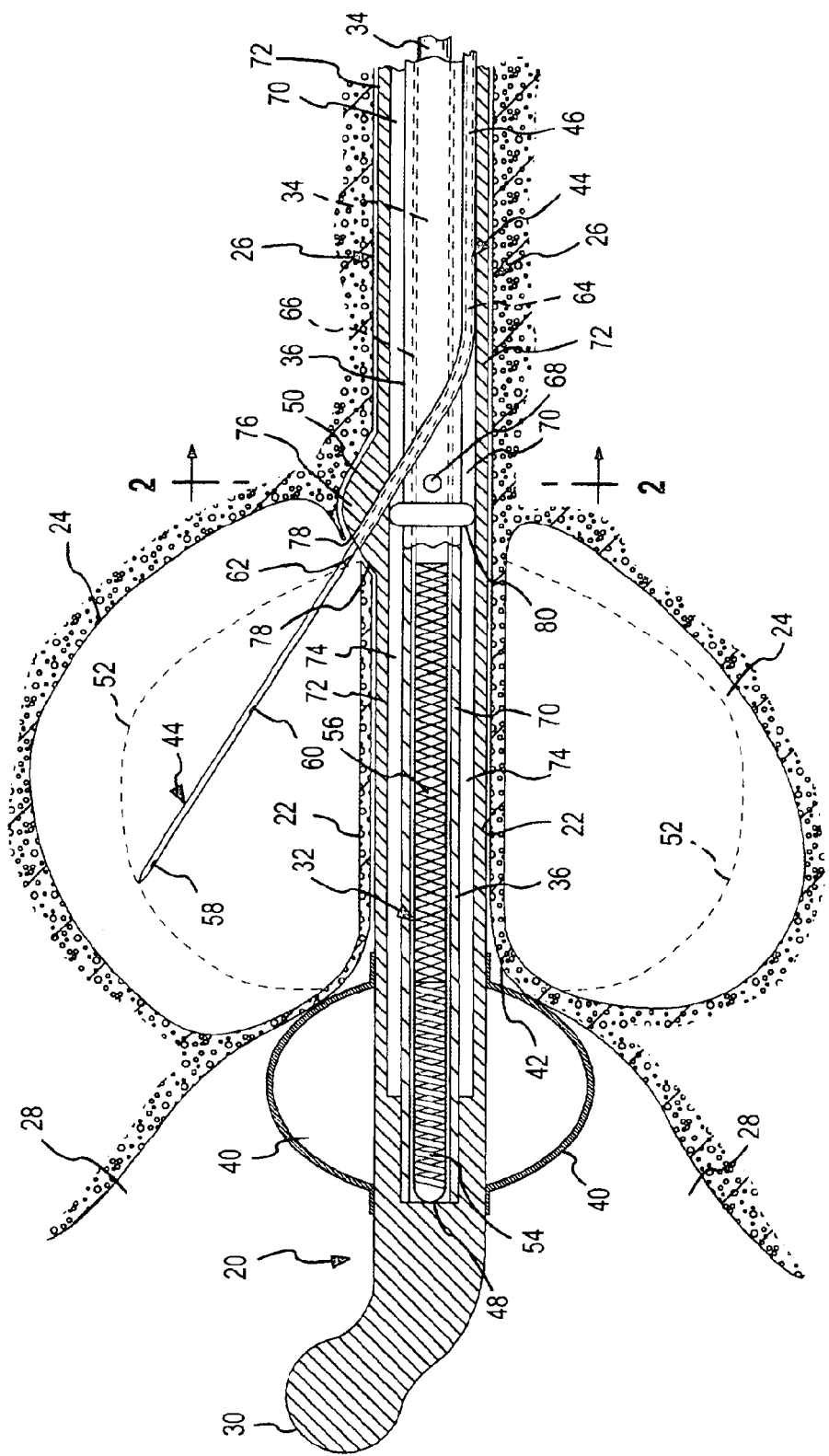
FIG. 1 is a partial longitudinal cross section view of the distal end of a microwave thermotherapy catheter embodying the present invention, with the catheter shown inserted in a urethra and a bladder of a male human.

A microwave thermotherapy catheter 20, which embodies the present invention, is shown in FIG. 1 positioned within a prostatic urethra 22. The prostatic urethra 22 is so named because it that portion of the entire urethra 26 (only partially shown) which is surrounded by a prostate gland 24. The entire urethra 26 extends from a bladder 28 through the penis of a male human to an exterior opening (none of which are shown). Urine drains from the bladder 28 under the control of the sphincter muscles (not shown) which are located adjacent to the prostate gland 24 on the opposite sides of the prostate gland 24.

The catheter 20 is inserted at a proximal location from the exterior opening of the urethra 26, until a distal tip end 30 of the catheter 20 is located within the bladder 28. A microwave antenna 32 attached at the distal end of an electrical feed coaxial cable 34 is inserted at the proximal end of the catheter 20 through a device or antenna guide tube 36, until the microwave antenna 32 contacts the distal tip end 30 of the catheter at the distal terminus of the guide tube 36. The tip end 30 of the catheter 20 includes a conventional inflatable balloon 40. The balloon 40 is deflated when the catheter 20 is inserted in the urethra 26. Passageways (not shown) extend from the interior of the balloon 40 to the distal end of the catheter 20. Fluid is inserted through the passageways to inflate the balloon 40, once it is located within the bladder 28.

The catheter 20 is then pulled proximally from the exterior of the human until the inflated balloon 40 contacts a neck 42 of the bladder 28 which surrounds the opening of the prostatic urethra 22. When inflated, the balloon 40 is too large to pass from the bladder 28 into the prostatic urethra 22. With the inflated balloon 40 contacting the bladder neck 42, the catheter 20 is located in the desired position for treating the prostate gland 24, as shown in FIG. 1.

After the catheter 20 has been located by contacting the inflated balloon 40 with the bladder neck 42, a temperature probe 44 is pushed through a probe guide tube 46 of the catheter 20 from a proximal location at the exterior of the urethra 26. The temperature probe 44 includes a needle-like tip end 48. Continued distal movement of the temperature probe 44 causes the tip end 48 to move out of an opening in a distal end portion 50 of the probe guide tube 46 and into the prostate gland 24. The distal movement of the temperature probe 44 continues until it reaches an extended position, as shown in FIG. 1. The penetration of the temperature probe 44 into the prostate gland 24 continues substantially in the direction established by the angle of the distal end portion 50 of the guide tube 46 relative to the axis of the catheter 20.

The coaxial cable 34 conducts electrical power at a microwave frequency to the antenna 32. The microwave frequency electrical power is supplied by a microwave generator (not shown) connected at a proximal end of the coaxial cable 34 at the exterior of the human. The antenna 32 broadcasts or radiates the microwave energy it receives from the cable 34 into the surrounding prostate gland 24. The radiated microwave energy interacts with the tissue of the prostate gland 24 and heats that tissue in a SAR or heating pattern generally indicated at 52. The heating pattern 52 is dependent upon the amount of electrical power supplied to the antenna 32, and the broadcast pattern established by the characteristics of the antenna 32.

The microwave antenna 32 shown in FIG. 1 is representative of a modified dipole antenna, in which one of its poles is formed by a helical coil 54, formed by coiling the conventional center conductor of the coaxial cable 34, and the other pole is formed by a folded back portion 56 of the conventional shielding screen of the coaxial feed cable 34. This modified dipole antenna 32 creates a focused SAR pattern 52 at the center of the prostate gland 24. Other antenna configurations are known and can be employed depending upon the type of heating pattern desired.

The temperature probe 44 preferably has a plurality of temperature sensors 58, 60, 62 and 64 positioned at locations spaced proximally from the tip end 48 of the temperature probe 44 and from one another. First, second and third temperature sensors 58, 60 and 62, respectively, are located at the distal portion of the temperature probe 44 which enters the prostate gland 24 when the temperature probe 44 is advanced to its extended position shown in FIG. 1. The three temperature sensors 58, 60 and 62 should occupy anticipated positions relative to the SAR or heating pattern 52. The different positions relative to the heating pattern 52 are established by the angle at which the distal portion of the temperature probe 44 penetrates into the prostate gland 24. The first temperature sensor 58 is near the distal tip end 48 of the temperature probe 44 and is farthest from the catheter 20 at a position to sense the temperature of the tissue at approximately the peak penetration point of the heating pattern 52. The second sensor 60 is located at an intermediate position within the heating pattern 52, and the third sensor 62 is located adjacent to the edge of the heating pattern 52 near the point where the temperature probe 44 enters the prostate gland 24, closest to the catheter 20. Signals from the temperature sensors 58, 60 and 62 are conducted through the temperature probe 44 to a computer (not shown) which interprets and processes the temperature signals to provide information to the surgeon concerning the extent and progress of the heating within the prostate gland 24.

The fourth temperature sensor 64 is located at a position on the temperature probe 44 within the probe guide tube 46, when the temperature probe 44 is moved to its extended position shown in FIG. 1. The interior diameter or cross sectional size of the antenna guide tube 36 is larger than the exterior cross section of the coaxial cable 34, as shown in FIG. 2. Thus, a generally concentric or annulus-like passageway 66 exists between the exterior of the coaxial cable 34 and the interior of the antenna guide tube 36.

Cooling liquid enters the passageway 66 from an opening or hole 68 formed in the antenna guide tube 36, and flows from the hole 68 proximally along the length of the passageway 66 surrounding the coaxial cable 34. The cooling fluid flowing in the passageway 66 removes heat generated by losses in the coaxial cable 34 when it conducts the microwave energy to the antenna 34. The heat from the coaxial cable 34 might be sufficient to damage or kill the healthy tissue of the urethra 26 or the penis. The fourth temperature sensor 64 senses the temperature of the cooling liquid, and signals from the sensor 64 indicate the temperature of the cooling liquid. An elevated temperature of the cooling liquid will require the amount of treatment power to be reduced or the flow rate of the cooling liquid to be increased.

The exterior cross section of the antenna guide tube 36 is smaller than the interior cross section of an outer tube 72 which generally defines the exterior of the catheter 20, as shown in FIG. 2. A concentric chamber 70 is generally defined by the annulus between the interior surface of the outer tube 72 and the exterior surface of the antenna guide tube 36. The concentric chamber 70 extends substantially the full length of the catheter 20. Thus, the concentric chamber 70 surrounds antenna guide tube 36 at positions adjacent to both the microwave antenna 32 and the coaxial cable 34.

Cooling liquid enters the concentric chamber 70 at the proximal end of the catheter 20. The cooling liquid flows distally from the proximal end of the catheter and ultimately fills the entire concentric chamber 70. Liquid from the concentric chamber 70 enters the hole 68 and flows distally within the passageway 66. Liquid is removed from the catheter 20 at the proximal end of the passageway 66. Consequently, a liquid flow path exists from the proximal end of the concentric chamber 70 through the hole 68 and back to the proximal end of the passageway 66. This liquid circulation path cools the coaxial cable 34.

Although the liquid fills a portion 74 of the concentric chamber 70 at locations adjoining the microwave antenna 32, no circulation of liquid occurs at this portion 74 of the concentric chamber 70. Instead, the liquid is still at these locations, and thus the portion 74 of the concentric chamber 70 functions as a still liquid chamber. Liquid does not circulate within the still liquid chamber 74 because there is no entrance and exit within the still liquid chamber 74. The only flow path into the passageway 66 is through the hole 68, and that hole 68 diverts the flow of liquid away from the still liquid chamber 74. In a similar manner, any liquid that may surround the antenna 32 within the antenna guide tube 36 is also not able to circulate for the same reasons. However, liquid does fill the still liquid chamber 74 and the area surrounding the microwave antenna 32 because of natural seepage as a result of the circulating liquid flow from the concentric chamber 70 through the hole 68 and into the passageway 66. The liquid which surrounds the antenna 32 and is within the still liquid chamber 74 effectively couples radiated energy from the antenna 32 into the surrounding tissue of the prostate gland 24.

Figure 4:
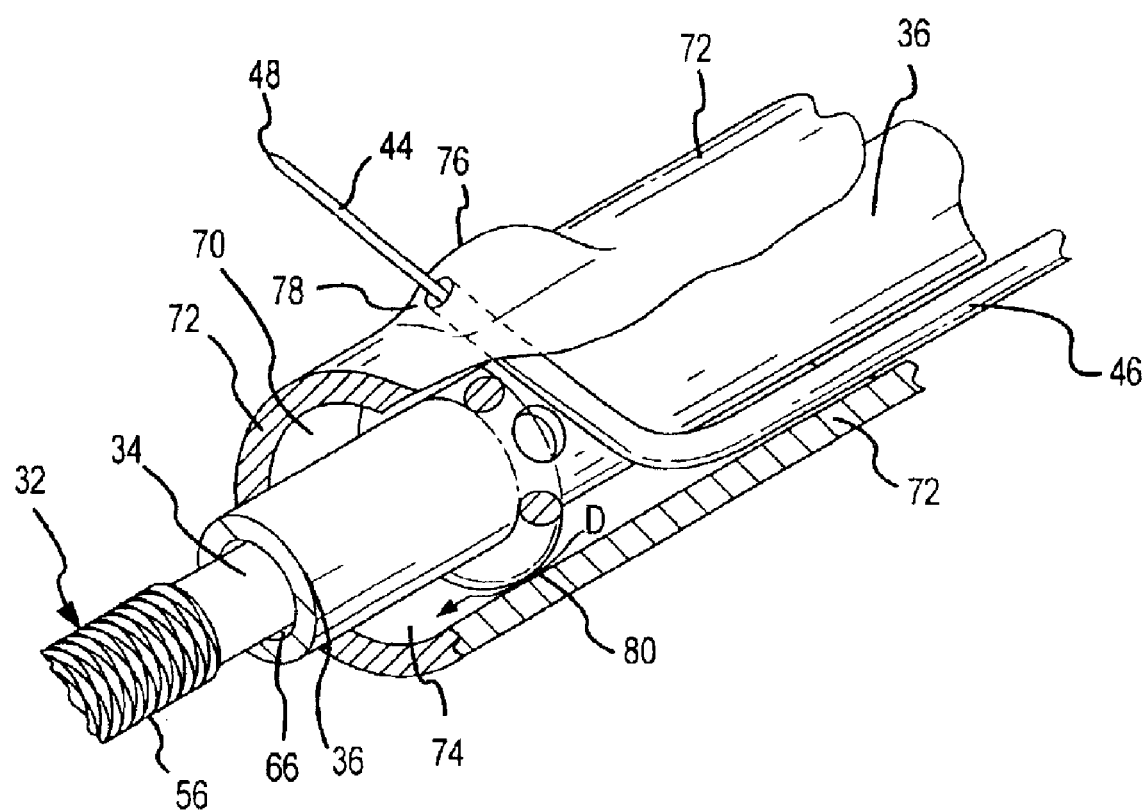
FIG. 4 is a cut-away perspective view of a portion of the catheter shown in FIG. 1 at approximately the location shown in FIG. 3.

The probe guide tube 46 is located within the concentric chamber 70 between the interior sidewall of the outer tube 72 and the exterior wall of the antenna guide tube 36, as shown in FIGS. 2–4. All but the distal end portion 50 of the probe guide tube 46 extends essentially parallel to the antenna guide tube 36. The distal end portion 50 of the probe guide tube 46 curves around the antenna guide tube 36 as it passes almost diagonally from one side of the concentric chamber 70 to the other side. The distal end portion 50 of the probe guide tube 46 opens through the outer tube 72 of the catheter 20 at a nodule 76, as shown in FIGS. 1, 3 and 4. The nodule 76 has a face 78 which extends at an angle to the axis of the catheter 20. The opening from the probe guide tube 46 is flush with the face 78 as shown in FIGS. 3 and 4.

The angle of the distal end portion 50 of the probe guide tube 46 relative to the axis of the catheter establishes the angle at which the temperature probe 44 exits from the catheter 20 and enters the tissue of the prostate gland 24, as understood from FIGS. 1, 3 and 4. By establishing and maintaining the angle of the distal end portion 50 of the probe guide tube 46 within the concentric chamber 70, the position of the temperature probe 44 within the prostate tissue is likewise established at the predetermined desired angular relationship upon which the tissue heating and tissue destruction information is based and calculated. The tissue heating and tissue destruction information is calculated from the signals representative of the temperature sensed by the sensors 58, 60 and 62. The tissue destruction and tissue heating calculations are based on the assumption that the temperature probe 44 extends at the predetermined angle. To the extent that the temperature probe 44 does not extend at this predetermined angle, the tissue heating and tissue destruction information will not be as accurate. Thus, it is advantageous to assure that the distal end portion 50 of the probe guide tube 46 angles to advance the temperature probe 44 into the prostate gland at the desired predetermined angle.

Substantial improvements are obtained in the catheter 20 as a result of using an O-ring 80, as shown in FIGS. 1, 3 and 4. The O-ring 80 is effective in establishing and assuring the desired angle of the distal end portion 50 of the probe guide tube 46. The O-ring 80 is positioned around the antenna guide tube 36 at the position slightly distal of the hole 68 in the antenna guide tube 36. In this surrounding position, the O-ring 80 is substantially connected to and retained relative to the antenna guide tube 36 particularly when the antenna 32 and the coaxial cable 34 are located within the interior of the antenna guide tube 36. The distal end portion 50 of the probe guide tube 46 rests against the O-ring 80 while being held in that position by the connection to the nodule 76. The stable support from the O-ring 80 surrounding the antenna guide tube 36 with the inserted antenna 32 and coaxial cable 34 is very effective in establishing and maintaining the angular orientation of the distal end portion 50 of the probe guide tube 46 so that the temperature probe 44 projects into the tissue of the prostate gland 24 at the desired and predetermined angle upon which the tissue heating and tissue destruction calculations are based.

Even though the support from the O-ring 80 creates significant stability for the distal end portion 50 of the probe guide tube 46, the O-ring 80 does not diminish the flexibility of the catheter 20 when it is inserted through the urethra 26. The antenna 32 and the coaxial cable 34 are not inserted in the antenna guide tube 36 when the catheter 20 is inserted in the urethra, so the O-ring 80 may deflect slightly itself or relative to the hollow antenna guide tube 36.

The O-ring 80 is also beneficial in confining the heated liquid in the still liquid chamber 74. Small gaps exist between the exterior of the O-ring 80 and the inside surface of the outer tube 72, and the small gaps are sufficient to allow the still liquid chamber 74 to fill with liquid, as shown by arrows in FIG. 3. The liquid in the still liquid chamber 74 becomes hot from conductive losses of the microwave antenna 32 when it radiates energy. The O-ring 80 effectively confines the heated liquid within the still liquid chamber 74. The increased thermal energy of the liquid in the still liquid chamber 74 is transferred by conduction through the outer tube 72 into the adjacent tissue of the prostate gland 24. The additional thermal energy transferred into the tissue of the prostate gland occurs at the location where tissue necrosis is desired. Consequently, the added thermal contribution from the heated liquid within the still liquid chamber 74 beneficially advances the treatment of the adjacent tissue of the prostate gland 24 because the added thermal energy contributes to tissue necrosis. In addition to preventing thermal interaction with the circulating cooling liquid, the O-ring 80 also maintains temperature of the heated liquid in the still liquid chamber 74 because it creates a barrier to thermal transfer of the heat to the circulating cooling liquid. Thus, the O-ring 80 also contributes to the heat treatment.

A presently preferred embodiment of the microwave thermotherapy catheter 20 has been described with a degree of particularity. Similar detailed descriptions have also been made of the improvements available from the O-ring, including establishing and maintaining a desired predetermined angular orientation of the temperature probe 44 into the prostate gland 24 and confining and applying the heat energy from the heated liquid in the still liquid chamber 74 to enhance tissue necrosis in the prostate gland 24. The particularity of these descriptions should not be construed as limiting the scope of the invention, since it is intended that the scope of the invention be defined by the following claims.

The invention claimed is:

1. In a thermotherapy catheter comprising an elongated outer tube extending from a proximal location of the catheter to a distal end of the catheter, a device guide tube positioned within the outer tube and separated from the outer tube by an annulus-like chamber and extending from the proximal location to the distal end of the catheter, the device guide tube defining an interior space for accepting a heat generating device and a connected feed cable of, the device guide tube positioning the heat generating device adjacent to the distal end of the catheter with the feed cable extending proximally from the heat generating device through the device guide tube to the proximal location of the catheter, the feed cable separated from the device guide tube by an annulus-like passageway, an opening extending through the device guide tube to create a flow path between the chamber and the passageway at a predetermined location located near a distal end of the feed cable, the opening permitting circulation of a cooling liquid within the chamber from the proximal location of the catheter and through the opening and into the passageway and from the passageway to the proximal location of the catheter, a probe guide tube located within the chamber and extending from the proximal location to an exit position located proximal from the distal end of the catheter at approximately the location of the connection of the heat generating device to the feed cable, the probe guide tube defining an interior space within which to receive an elongated temperature probe which includes a tip end which is movable out of the probe guide tube at the exit position and through the outer tube, the probe guide tube including a distal end portion which angles transversely within the chamber to establish an acute angle relative to the longitudinal extent of the catheter when the tip end of the temperature probe moves out of the catheter at the exit position; and an improvement comprising:

a contact member positioned within the chamber at a position distal of the opening and extending between the device guide tube and the outer tube, the contact member further positioned to contact the distal end portion of the probe guide tube at a location adjacent the exit position, the contact of the contact member with the distal end portion of the probe guide tube supports the distal end portion of the probe guide tube to maintain the established acute angle.

2. A catheter as defined in claim 1, wherein:

the contact member further separates the chamber into a still liquid chamber located distally of the contact member and a flow path for the cooling liquid located proximally of the contact member.

3. A catheter as defined in claim 2, wherein:

the contact member permits liquid to seep from the flow path into the still liquid chamber.

4. A catheter as defined in claim 3, wherein:

the contact member contacts the outer tube in a non-integrally and non-sealed manner.

5. A catheter as defined in claim 4, wherein:

the contact member comprises an O-ring which surrounds and contacts the device guide tube and the outer tube.

6. A catheter as defined in claim 5, wherein:

the contact member permits the liquid to seep past the location where the O-ring contacts the outer tube.

7. A catheter as defined in claim 3, wherein:

the contact member creates a thermal barrier between the still liquid chamber and the cooling liquid flow path.

8. A catheter as defined in claim 1, wherein:

the contact member occupies the chamber between the device guide tube and the outer tube.

9. A catheter as defined in claim 8, wherein:

the contact member comprises an O-ring.

10. A catheter as defined in claim 1, wherein:

the contact member comprises an O-ring seated against and surrounding the device guide tube, the O-ring further concentrically contacting the outer tube, and the O-ring further contacting the distal end portion of the probe guide tube at the exit position.

11. A catheter as defined in claim 10, wherein:

the O-ring separates the chamber into a still liquid chamber located distally of the O-ring and a flow path for the cooling liquid located proximally of the O-ring; and the O-ring permits liquid to seep from the flow path into the still liquid chamber.

12. A catheter as defined in claim 1, further comprising in combination:

a heat generating device and a connected to a feed cable positioned within the interior space of the device guide tube.

13. A catheter as defined in claim 12, wherein:

the heat generating device comprises a microwave emitting antenna, and the feed cable comprises a coaxial cable for conducting microwave electrical energy to the antenna.

14. A catheter as defined in claim 1, further comprising in combination:

an elongated temperature probe which includes a tip end which is adapted to penetrate into tissue when the temperature probe is moved out of the probe guide tube at the exit position.

15. A catheter as defined in claim 1, further comprising in combination:

a source of circulating cooling liquid connected to the catheter at the proximal location and operative to introduce cooling liquid into the chamber at the proximal location and to remove cooling liquid from the passageway at the proximal location.

16. A method of heat treating a prostate gland using a catheter, the prostate gland surrounding a prosthetic urethra portion of a urethra which extends from a bladder to an exterior of a male human, the catheter comprising an elongated outer tube extending from a proximal location of the catheter to a distal end of the catheter, a device guide tube positioned within the outer tube and separated from the outer tube by an annulus-like chamber and extending from the proximal location to the distal end of the catheter, the device guide tube defining an interior space, a probe guide tube located within the chamber and extending from the proximal location to an exit position located proximal from the distal end of the catheter, the probe guide tube including a distal end portion which angles transversely within the chamber to establish an acute angle relative to the longitudinal extent of the catheter, the probe guide tube defining an interior space, an opening extending through the device guide tube between the interior space of the device guide tube and the chamber at approximately the location of the exit position, and a contact member positioned within the chamber at a position distal of the opening and extending between the device guide tube and the outer tube, the contact member further positioned to contact the distal end portion of the probe guide tube at a location adjacent the exit position; said method comprising:

inserting the catheter in the urethra from the exterior of the human;

locating the inserted catheter at a predetermined position within the urethra relative to the bladder;

inserting a heat generating device and a connected feed cable within the interior space of the device guide tube until the heat generating device adjoins the prostate gland;

extending the feed cable proximally from the heat generating device through the interior space of the device guide tube to the proximal location of the catheter;

separating the feed cable from the device guide tube by an annulus-like passageway which communicates with the opening;

increasing resistance to bending of the device guide tube by inserting the heat generating device and connected feed cable into the interior space of the device guide tube;

maintaining the acute angle of the distal end portion of the probe guide tube by the contact member contacting the distal end portion of the probe guide tube and the device guide tube after the heat generating device and feed cable have been inserted;

inserting a temperature probe into the probe guide tube from the proximal location until a distal end of the temperature probe extends from the exit location through the outer tube and penetrates into the prostate gland at the acute angle of the distal end portion of the probe guide tube maintained by the contact member;

separating the chamber into a still liquid chamber located distally of the contact member and a flow path for cooling liquid located proximally of the contact member;

flowing cooling liquid in a circulatory flow path within the chamber and the passageway and through the opening;

filling the still liquid chamber with liquid from the circulatory flow path;

substantially confining the liquid within the still liquid chamber against movement out of the still liquid chamber; and delivering energy through the feed cable to the heat generating device to generate heat for heat treating the prostate gland.

17. A method as defined in claim 16, further comprising:

flowing cooling liquid in the circulatory flow path by introducing the cooling liquid in the chamber at the proximal location of the catheter, flowing the cooling liquid distally through the chamber to the opening, flowing the cooling liquid through the opening into the passageway, flowing the cooling liquid proximally within the passageway to the proximal location of the catheter, and removing the cooling liquid from the passageway at the proximal location of the catheter.

18. A method as defined in claim 16, wherein the temperature probe includes a plurality of temperature sensors positioned at the distal end of the temperature probe, and said method further comprises:

moving the temperature probe until the distal end of the temperature probe has penetrated into the prostate gland a sufficient distance to locate at least two of the temperature sensors within the prostate gland.

19. A method as defined in claim 16, wherein the heat generating device comprises a microwave emitting antenna and the feed cable comprises a coaxial cable, and said method further comprises:

conducting microwave electrical energy through the coaxial cable to the antenna; and emitting microwave radiation into the prostate gland from the antenna.

20. A method as defined in claim 16, wherein the contact member is an O-ring, and said method further comprises:

seating the O-ring against and surrounding the device guide tube;

concentrically contacting the O-ring with the outer tube;

contacting the distal end portion of the probe guide tube at the exit position with the O-ring;

locating the O-ring to separate the chamber into the still liquid chamber and the circulatory flow path; and seeping liquid from the circulatory flow path past the O-ring to fill the still liquid chamber.

* * * * *